United States Patent

Nomoto et al.

[11] Patent Number: 5,973,777
[45] Date of Patent: Oct. 26, 1999

[54] METHOD AND APPARATUS FOR INSPECTING DEFECTS OF SURFACE SHAPE

[75] Inventors: Mineo Nomoto, Yokohama; Takanori Ninomiya, Hiratsuka; Yuji Takagi, Yokahama, all of Japan

[73] Assignee: Hitachi, Ltd., Tokyo, Japan

[21] Appl. No.: 08/880,543

[22] Filed: Jun. 23, 1997

[30] Foreign Application Priority Data

Jun. 25, 1996 [JP] Japan .................................. 8-164391

[51] Int. Cl.⁶ .......................... G01N 21/00; G01B 11/30; G01B 11/24
[52] U.S. Cl. .................................. 356/237.5; 356/237.6; 356/371; 356/376
[58] Field of Search ............................. 356/237.3–237.6, 356/376, 371, 375, 394

[56] References Cited

U.S. PATENT DOCUMENTS 5,636,023  6/1997  Yanagisawa ........................... 356/376

FOREIGN PATENT DOCUMENTS 62-127614  6/1987  Japan .
1-250705  10/1989  Japan .
2-73139   3/1990  Japan .
4-134255  5/1992  Japan .
5-29420   2/1993  Japan .

*Primary Examiner*—Robert H. Kim
*Assistant Examiner*—Amanda Merlino
*Attorney, Agent, or Firm*—Antonelli, Terry, Stout & Kraus, LLP

[57] ABSTRACT

In order to detect a local shape defect on an inner surface of an ordinary plane member with a high degree of accuracy as a state distinguished from a big waviness deformation, a surface-shape-defect inspecting method and apparatus for identifying the shape defect on the inner surface of the plane member is provided. The method and apparatus provides for scanning optically the entire area of the plane member, extracting a shape of the surface of the plane member as absolute height displacement data at scanning positions, finding a difference between a reference surface shape inferred from the extracted shape of the surface of the plane member and the shape of the surface, and using the difference as relative height displacement data with respect to the reference surface shape, and detecting the shape defect on the surface by identifying the location of the shape defect through comparison of the relative height displacement data with predetermined allowable displacement.

38 Claims, 9 Drawing Sheets

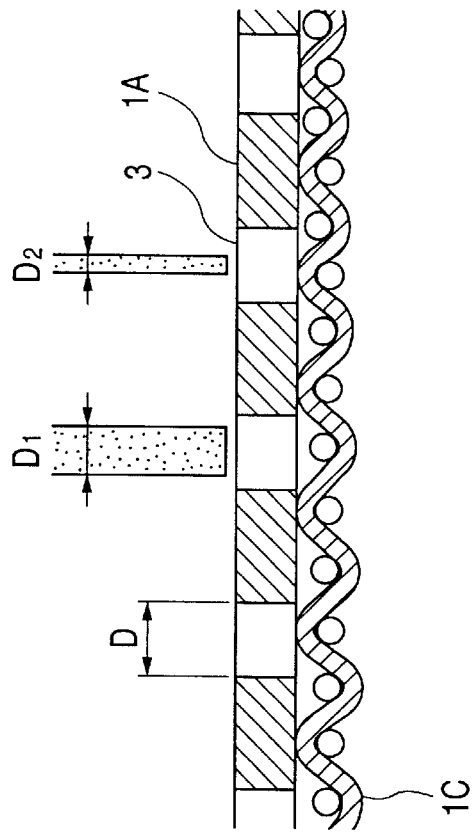
FIG. 4(A)
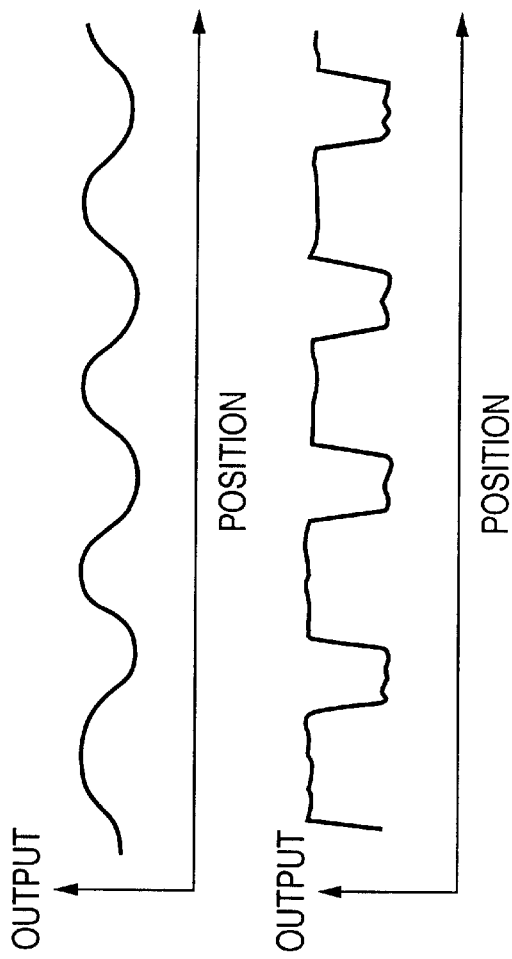
FIG. 4(B)
FIG. 4(C)

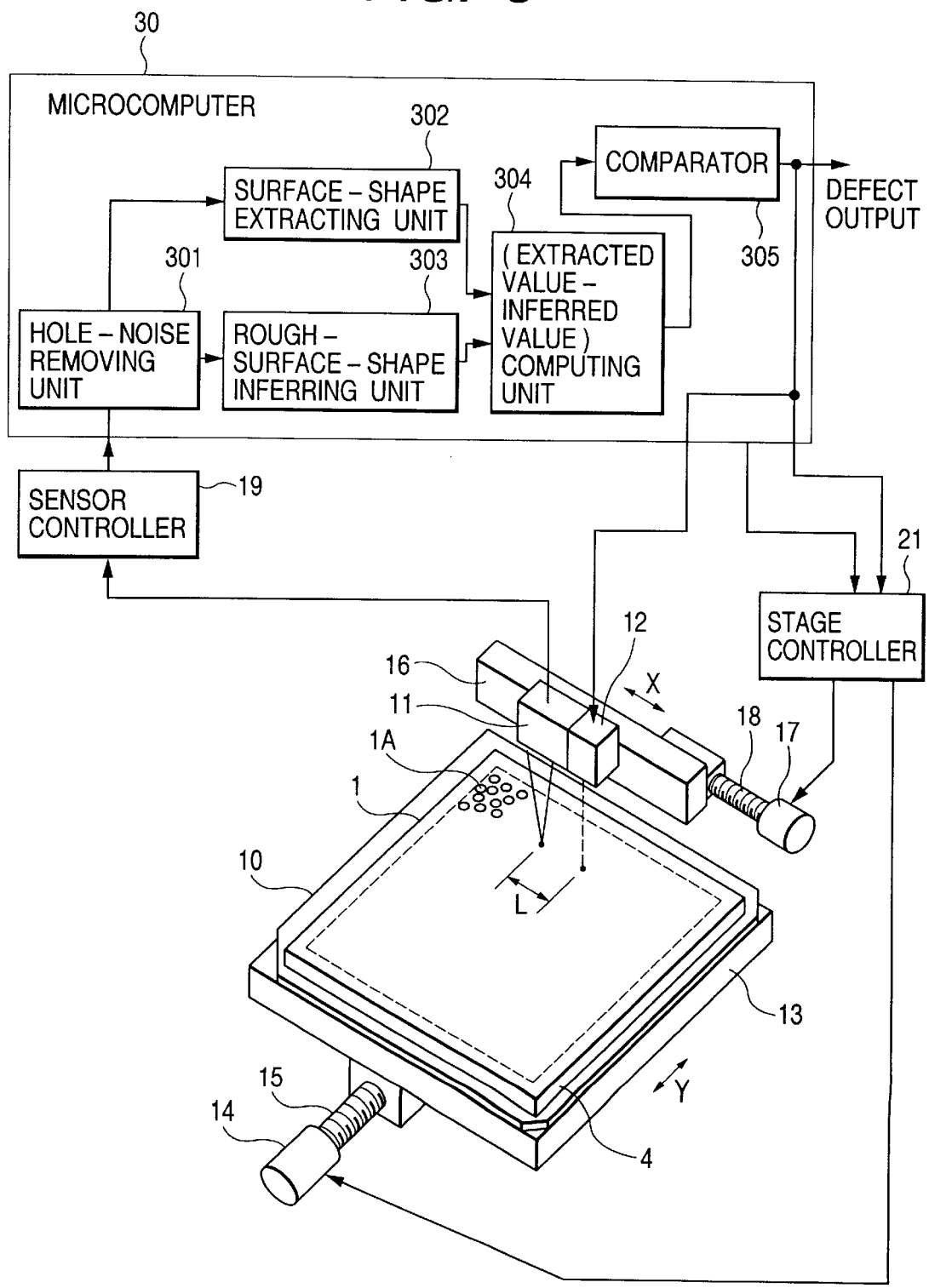

METHOD AND APPARATUS FOR INSPECTING DEFECTS OF SURFACE SHAPE

BACKGROUND OF THE INVENTION

The present invention relates to a surface-shape-defect inspecting method and its apparatus for optically detecting shape defects of an internal surface of a plane member with its circumference composed of a member having good rigidity and shape defects of a surface of a plane member having a thin and plane plate shape such as a mask used as a screen for printing a circuit pattern and semiconductor paste in a process of manufacturing devices such as an electronic-circuit board and hybrid ICs by identifying positions of the shape defects.

FIG. 7 is a skeleton diagram showing a squint view of an apparatus for printing a circuit pattern or semiconductor paste on a substrate by using a screen 1. As shown in the figure, the screen 1 is provided with an external frame 4 built along the circumference thereof as a single assembly in order to make the screen 1 rigid and the work to handle the screen 1 easy to do. It should be noted that the screen 1 is a thin plane plate member made of a nickel plate 2 with a thickness of several tens of microns and pattern holes 3 are bored through it in an etching process. When necessary, a knitted-in mesh described below is attached to the screen 1 itself. In the case of a screen for creating a pattern with a large numerical aperture or the like, by attaching a knitted-in mesh made of stainless wires each with a diameter of several tens of microns, the strength of the screen 1 as a whole can be enhanced depending upon the shape of the pattern.

When screen printing is carried out by the screen 1 having a configuration described above, while ink 6 in a paste or liquid state is being rubbed on the screen 1 by using brush hair called squeegee 5, the ink 6 is pushed out from the pattern holes 3 so that a pattern 9 determined by the shape of the pattern holes 3 is transferred to substrate 8 mounted on the holder 7.

By the way, in a screen printing process, the screen itself is required to have highly accurate flatness for a reason to be described later. Thus, it is necessary to check the flatness of the screen itself prior to the screen printing. These requirements also apply to a plane member for a special purpose other than the screen even if no pattern holes are bored through the plane member.

It should be noted that, so far, surface shapes and defects of a plane member for example are inspected and detected in order to achieve some objectives. A method for detecting the unevenness displacements of the surface of a plane member is disclosed in documents such as Japanese Patent Laid-open No. Sho62-127614. According to this method, a laser beam radiated by a semiconductor laser is applied to a work surface by way of a radiation-side light converging lens while a light reflected by the work surface is detected by a detector through a light converging lens on the light-receiving side. A work-surface displacement is detected from the light receiving position on the detector. According to a method disclosed in Japanese Patent Laid-open No. Hei1-250705, on the other hand, predetermined processing is carried out to measure the shape of the three-dimensional surface, an object of measurement. An example of the predetermined processing is scanning by a line-shaped slit light along straight lines over the entire area of the three-dimensional surface.

Even if a large waviness deformation on a screen as a whole can be corrected during an operation to transfer a circuit pattern to a substrate by using a squeegee, screen printing is carried out with local deformations and uneven portions existing on the screen by keeping their deformed states as they are. As a result, in actuality, the improvement of the printing accuracy can not be expected.

This is because gaps are formed inevitably between the screen and the surface of the substrate subjected to printing, losing a state of adherence during the printing operation. As a result, it is feared that the accuracy and reliability of the printing on a printed matter is lost, causing printing blurs to be generated or the printed matter to be injured. In order to solve this problem, the surface of the screen which is used as a printing negative is required to have such excellent flatness that no local deformation or unevenness is formed on the surface, in particular, the surface of the side in direct contact with the printed matter. For this reason, it is thus necessary to take countermeasures wherein the flatness of the surface is evaluated in advance and local deformations and uneven portions found in the evaluation are corrected or an uncorrectable bad screen is discarded.

It should be noted that, in the case of a member with holes and/or openings for creating a pattern are formed on the surface thereof such as a mask used as a printing screen, with the methods disclosed in the documents described above, not only is it possible to measure waviness and unevenness on the surface of the member, but a large waviness deformation and a local deformation on the surface of the member can not even be identified.

SUMMARY OF THE INVENTION

It is thus a first object of the present invention to provide a surface-shape-defect inspecting method and its apparatus which are capable of detecting a local shape defect on the inner surface of an ordinary plane member as a state distinguished from a large waviness deformation with a high degree of accuracy.

It is a second object of the present invention to provide a surface-shape-defect inspecting method and its apparatus which are capable of detecting a local shape defect on the inner surface of an ordinary plane member with holes formed on the surface thereof as a state distinguished from a big waviness deformation without a need to scan the holes and with a high degree of accuracy.

It is a third object of the present invention to provide a surface-shape-defect inspecting method and its apparatus which are capable of detecting a local shape defect on the inner surface of an ordinary plane member having a configuration with holes formed on the surface thereof as a state distinguished from a big waviness deformation without being affected by the holes and with a high degree of accuracy.

It is a fourth object of the present invention to provide a surface-shape-defect inspecting method and its apparatus which are capable of detecting a local shape defect on the inner surface of an ordinary plane member having a configuration with a member having good rigidity provided along the circumference thereof as a state distinguished from a large waviness deformation with a high degree of accuracy.

It is a fifth object of the present invention to provide a surface-shape-defect inspecting method and its apparatus which are capable of detecting a local shape defect on the inner surface of an ordinary plane member having a configuration with a member having good rigidity provided along the circumference thereof and holes formed on the surface thereof as a state distinguished from a large waviness deformation without a need to scan the holes and with a high degree of accuracy.

It is a sixth object of the present invention to provide a surface-shape-defect inspecting method and its apparatus which are capable of detecting a local shape defect on the inner surface of an ordinary plane member having a configuration with a member having good rigidity provided along the circumference thereof and holes formed on the surface thereof as a state distinguished from a large waviness deformation without being affected by the holes and with a high degree of accuracy.

It is a seventh object of the present invention to provide a surface-shape-defect inspecting method and its apparatus which are capable of detecting a local shape defect on the inner surface of an ordinary plane member as a marked state at the position of the defect regardless of whether or not holes are formed on the surface of the plane member and at least regardless of whether or not a member having good rigidity is provided along the circumference without being affected by the holes, if any, and with a high degree of accuracy.

It is an eighth object of the present invention to provide a surface-shape-defect inspecting method and its apparatus which are capable of detecting a local shape defect on the inner surface of an ordinary plane member with holes formed on the surface thereof regardless of whether or not a member having good rigidity is provided along the circumference without being affected by the size of the holes and with a high degree of accuracy.

The methods adopted to achieve the objects described above basically each comprise the steps of:

scanning optically the entire area of the plane member;

identifying a shape of an inner surface of the plane member as absolute height displacement data at scanning positions of the inner surface;

finding a difference between a rough reference surface shape inferred specially from the shape of the inner surface of the plane member and the shape of the inner surface or a difference between a reference surface shape inferred specially from the external-circumference surface shape of a member having good rigidity provided on the circumference of the plane member and the shape of the inner surface, and using the difference as relative height displacement data with respect to the reference surface shape; and identifying the position of a shape defect on the inner surface by comparing the relative height displacement data with predetermined allowable displacement data.

The configurations of the apparatuses used to achieve the objects described above basically each comprise:

an absolute-height-displacement extracting means for identifying a shape of an inner surface of the plane member as absolute height displacement data at scanning positions of the inner surface by scanning optically the entire area of the plane member;

a reference-surface-shape inferring means for specially inferring a rough reference surface shape for the surface of the plane member from the shape of the surface of the plane member or for specially inferring a reference surface shape for the inner surface of the plane member from the external-circumference surface shape of a plane member having good rigidity provided on the circumference of the plane member;

a relative-height-displacement extracting means for finding a relative height displacement data by finding a difference between the reference surface shape inferred by the reference-surface-shape inferring means and the shape of the inner surface identified by the absolute-height-displacement extracting means; and a shape-defect identifying means for identifying the position of a shape defect on the inner surface by comparing the relative height displacement data found by the relative-height-displacement extracting means with predetermined allowable displacement data.

BRIEF DESCRIPTION OF THE DRAWINGS

Embodiments of the present invention will be explained with reference to the following figures wherein:

FIGS. 4(A)–4(C) are diagrams used for explaining a difference in resolution in examination of the shape of a surface caused by a difference in diameter of a scanning light beam;

FIG. 8 is a diagram showing a squint view of a configuration of a second embodiment implementing a surface-shape-defect inspecting apparatus provided by the present embodiment;

DETAILED DESCRIPTION OF THE PREFERRED EMBODIMENTS

Figure 1:
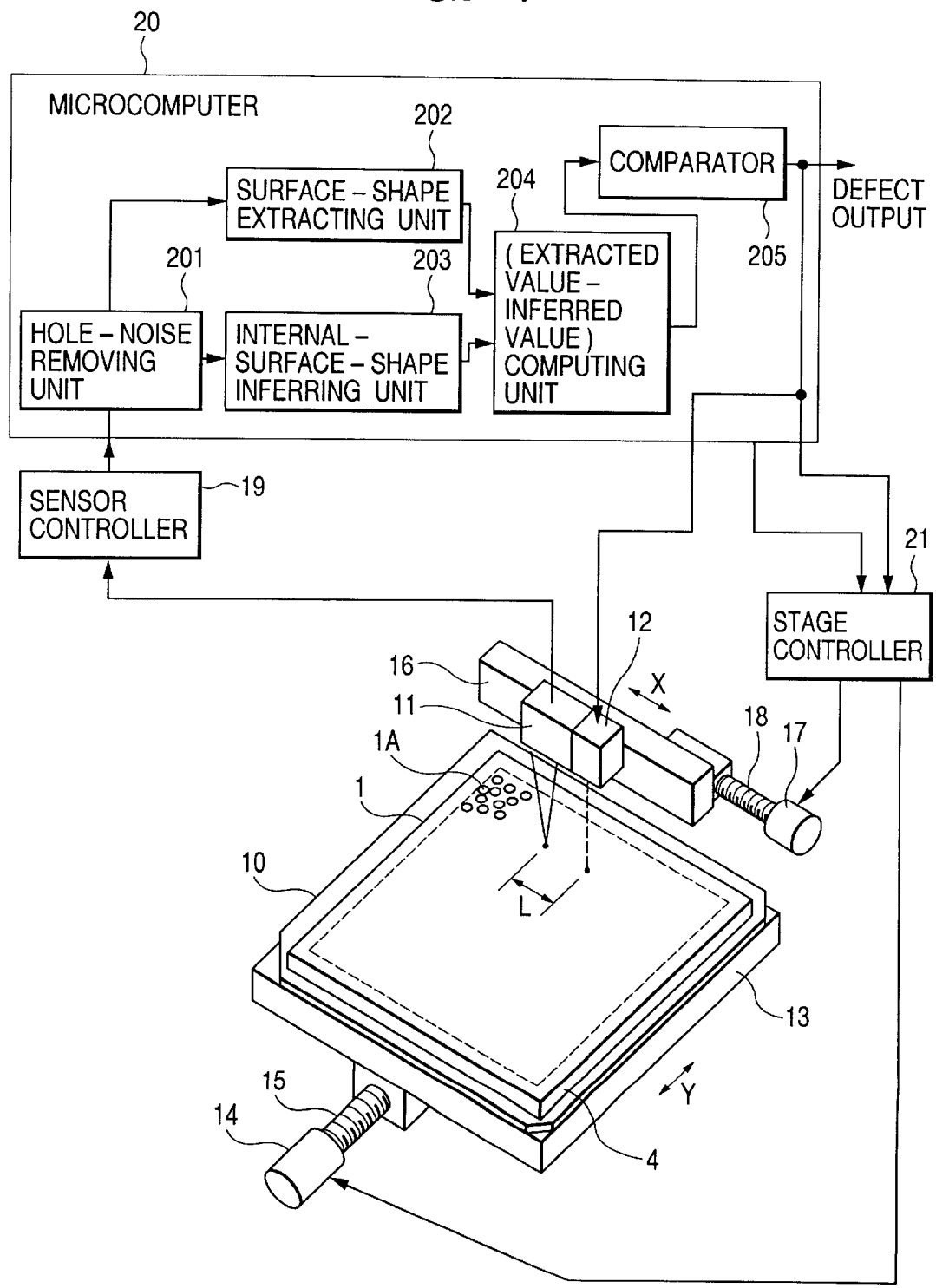
FIG. 1 is diagram showing a squint view of a typical configuration of a surface-shape-defect inspecting apparatus provided by the present invention.

The present invention will become more apparent from a study of the following detailed description of some preferred embodiments with reference to the accompanying diagrams some of which show the embodiments. The description begins with a first embodiment of the present invention to be explained with reference to FIGS. 1 to 7 wherein a screen with pattern holes bored through the surface thereof is taken as an example of a plane member. FIG. 1 is a diagram showing a squint view of a typical configuration of a surface-shape-defect inspecting apparatus implemented by the first embodiment of the present invention. The surface-shape-defect inspecting apparatus is used for detecting a shape defect on the surface of a screen with a configuration including a member having good rigidity provided on the circumference of the screen.

First of all, the typical configuration of a surface-shape-defect inspecting apparatus provided by the present invention is explained by referring to FIG. 1. The screen 1 itself, which serves as an object to undergo surface-shape-defect inspection, has an external frame 4 built along the circumference thereof as a single assembly, and is mounted on and held by a work holder 10. The work holder 10 can be moved back and forth in a Y scanning direction by a Y motor 14 and a feeding screw 15 which together drive a Y stage 13. Held by the work holder 10, the screen 1 can thus be moved back and forth in the Y scanning direction along with the work holder 10.

On the other hand, a detector 11 and a marking unit 12 are provided above the screen 1, being separated away from each other by a fixed distance L. Disclosed in Japanese Patent Laid-open No. Hei5-29420 is a typical detector 11 which adopts a light cutting technique. The detector 11 and the marking unit 12 are attached to and held by an X stage 16. Much like the Y stage 13, the X stage 16 can be moved back and forth in an X scanning direction by an X motor 17 and a feeding screw 18. Held by the X stage 16, the detector 11 and the marking unit 12 can thus be moved back and forth in the X scanning direction along with the X stage 16.

A microcomputer 20 controls a stage controller 21 which, in turn, moves the X stage 16 and the Y stage 13 in the X and Y scanning directions respectively. In this way, the surface 1A of the screen 1 is scanned optically by the detector 11. At the same time, variations in voltage representing the surface height shape generated by the detector 11 are supplied to the microcomputer 20 by way of a sensor controller 19 in synchronization with the scanning operation as absolute height displacement data at the corresponding scanning locations to undergo predetermined processing.

As shown in the figure, the microcomputer 20 comprises a hole/noise removing unit 201, a surface-shape extracting unit 202, an internal-surface-shape inferring unit 203, an (extracted value–inferred value) computing unit 204 and a comparator 205. First of all, the hole/noise removing unit 201 removes noise generated by pattern holes 3 and areas surrounding them from the absolute height displacement data at the corresponding scanning locations in accordance with the absolute height displacement data itself which is received sequentially from the detector 11. Then, the surface-shape extracting unit 202 extracts the shape of the surface 1A excluding the pattern holes 3 on the basis of the absolute height displacement data at the corresponding scanning locations on the surface 1A. In the mean time, while the shape of the surface 1A is being extracted, the internal-surface-shape inferring unit 203 infers a reference surface shape for the surface 1A on the screen 1 from absolute height displacement data of the external frame 4 provided on the circumference of the screen 1.

The (extracted value–inferred value) computing unit 204 then computes a difference between the shape of the surface 1A extracted by the surface-shape extracting unit 202 and the reference surface shape for the surface 1A inferred by the internal-surface-shape inferring unit 203, supplying the difference to the comparator 205 which compares the difference with a predetermined allowable value. A difference found greater than the allowable value indicates that a local surface-shape defect exists on the surface 1A at position coordinates (X, Y). In this case, the stage controller 21 moves the marking unit 12 to the location of the surface-shape defect at the coordinates (X, Y) by driving the X stage 16 and the Y stage 13. The location is then marked with something that allows the surface-shape defect to be seen with ease.

By the way, in the present example described above, the reference surface shape is inferred from actually measured data of the surface 1A each time such data is obtained. It should be noted that a reference surface shape based on design values can also be used. When a reference surface shape based on design data is used, the internal-surface-shape inferring unit 203 is used for storing the reference surface shape in advance.

Figure 2:
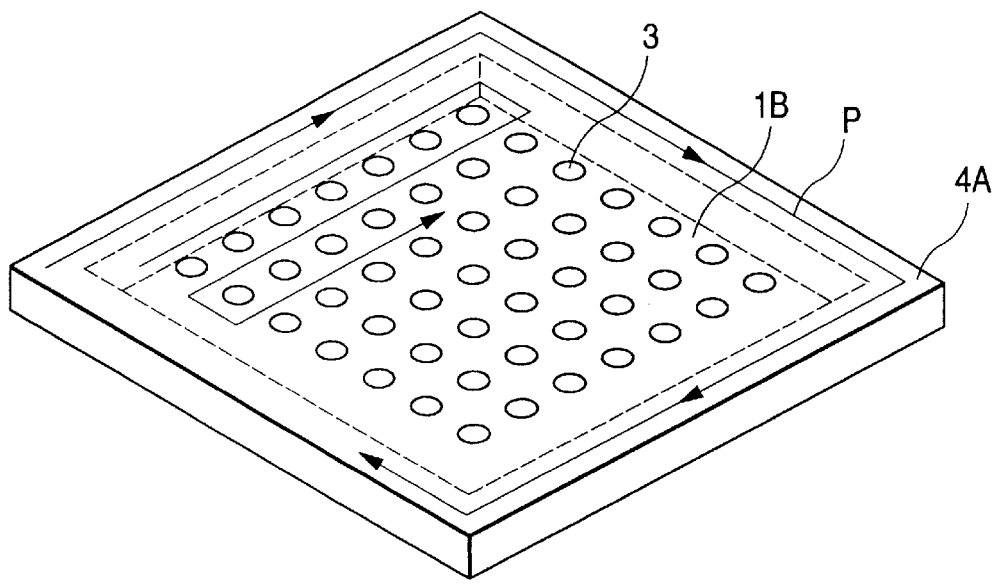
FIG. 2 is a diagram showing a squint view of a screen and a first scanning method for scanning the surface of the screen.
Figure 3:
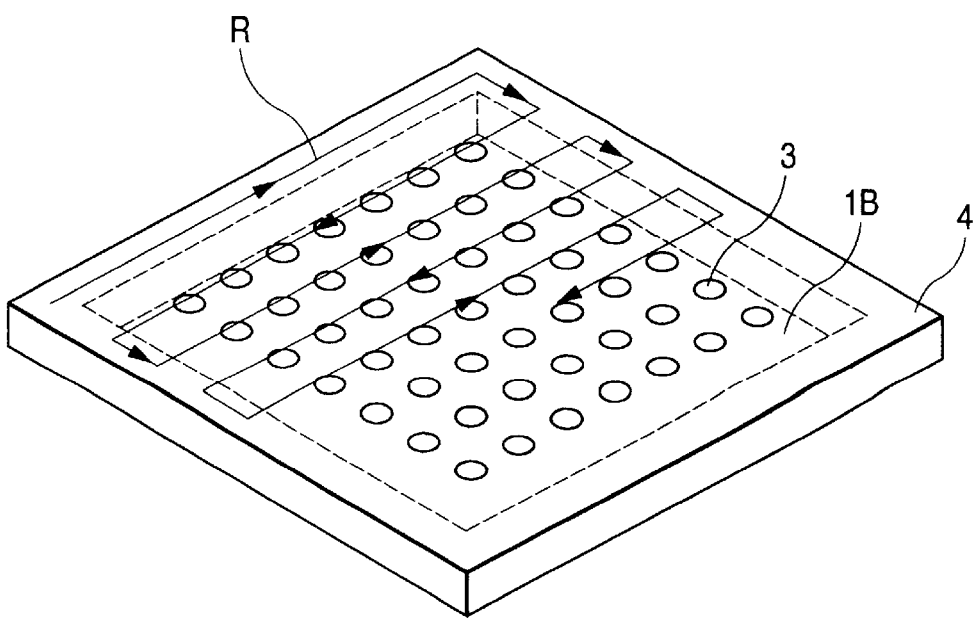
FIG. 3 is a diagram showing a squint view of a screen and a second scanning method for scanning the surface of the screen.

As described above, the surface 1A of the screen 1 is scanned by the detector 11. FIG. 2 is a diagram showing a squint view of the screen 1 and a first scanning method for scanning the entire surface of the screen 1 and FIG. 3 is a diagram showing a squint view of the screen 1 and a second scanning method for scanning the entire surface of the screen 1. First of all, the first scanning method shown in FIG. 1 is explained. According to this method, the external frame 4A provided on the circumference of the screen 1 is scanned in a direction indicated by an arrow P while the surface 1A of the screen 1 is scanned by avoiding pattern holes 3 in accordance with design data. As a result, only the surface 1A excluding the pattern holes, that is, only a surface 1B, is scanned.

In the case of the second scanning method shown in FIG. 3, on the other hand, the external frame 4 and the surface 1A of the screen 1 are scanned in a direction indicated by an arrow R without avoiding the pattern holes 3. In this method, the pattern holes 3 are scanned sequentially one after another. The first scanning method shown in FIG. 2 is particularly effective for a case in which the hole patterns 3 are arranged regularly. This method is adopted in a case where it is not necessary to consider changes in intensity of complicated lights reflected by edges of the pattern holes and a supporting mesh. The surface shape can be extracted on the basis of absolute height displacement data at scanning locations on the surface 1A.

FIG. 4A is a diagram showing part of a cross section of the screen 1. As described earlier by referring to FIG. 7, a knitted-in mesh 1C made of stainless wires each with a diameter of several tens of microns is attached to the surface on the printed-matter side of the screen 1. Notation D shown in FIG. 4A denotes the diameter of the pattern hole 3 and notations D1 and D2, where D1>0.5 D and D2<0.5 D, are diameters of scanning light beams radiated by the detector 11. When a light beam with the diameter D1 scans the pattern holes 3, the detector 11 outputs a signal with a waveform shown in FIG. 4B. When a light beam with the diameter D2 scans the pattern holes 3, on the other hand, the detector 11 outputs a signal with a waveform shown in FIG. 4C.

It is also obvious from FIG. 4B that, in the case of a large light-beam diameter, as an output from the detector 11, the output of a light reflected from a pattern hole 3 is superposed on the output of a light reflected by a flat portion of the surface 1A adjacent to the pattern hole 3. By the same token, the output of a light reflected by a flat portion of the surface 1A adjacent to a pattern hole 3 is superposed on the output of a light reflected from the pattern hole 3. As a result, the shape of the surface 1A can not be detected with a high degree of reliability as indicated by the waveform shown in FIG. 4B.

In the case of a small light-beam diameter, on the other hand, the output of a light reflected from a pattern hole 3 and the output of a light reflected by a flat portion of the surface 1A adjacent to the pattern hole 3 are not superposed on each other, making it possible to detect the shape of the surface 1A with a high degree of reliability as indicated by the waveform shown in FIG. 4C. In other words, the smaller the diameter of the scanning light beam in comparison with the size of the pattern hole 3, the higher the sensitivity of the detection of the surface shape.

In the case of this example, the diameter of the light beam radiated by using typically a light cutting method has been described. It should be noted, however, that the resolution of detection of a reflected light can be thought in the same way. That is to say, by making the size of one picture element on a television camera or a linear sensor smaller than the diameter of the pattern hole 3 or smaller than half the width of the hole, an equivalent effect can be obtained.

Figure 5A:
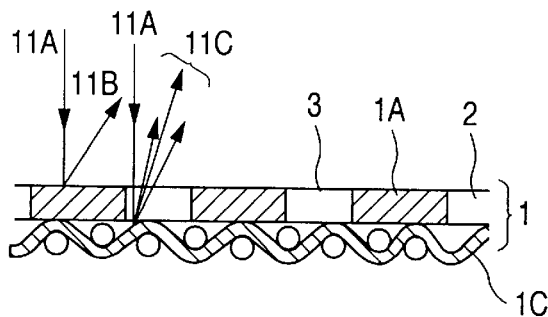
FIG. 5A is a diagram showing a cross section of a screen and FIGS. 5B to 5D are diagrams each showing a relation between the position on the cross-sectional diagram of FIG. 5A and the output of a sensor.

The following is description of the hole-noise removing process carried out by the hole-noise removing unit 201. FIG. 5A is a diagram showing part of the cross section of the screen 1. As shown in the figure, the shape of the pattern hole 3 varies steeply in comparison with the flat portion 1B. Let an optical displacement gage disclosed in Japanese Patent Laid-open No. Hei5-29420 be used as the detector 11. In this case, when the pattern hole 3 is scanned, a light beam 11B reflected by the flat portion 1B exhibits regularity with respect to a radiated light beam 11A. If the radiation position of the radiated light beam 11A is inclined or deformed, however, the light beam 11A from the inclined or deformed radiation position is reflected irregularly as lights 11C and, as a result, the shape of the surface can not be detected with a high degree of reliability.

Figure 5B:
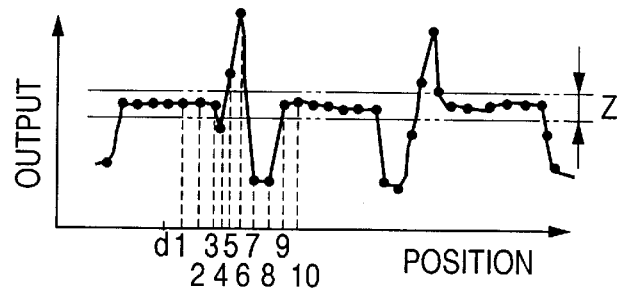

FIG. 5B shows the waveform of a signal output by the detector 11 as a result of scanning not only the flat portion 1B but also the pattern hole 3. It should be noted that black points on the waveform each denote a sampling point. The waveform then undergoes predetermined processing in the hole-noise removing unit 201. A final result of the processing is output as a waveform shown in FIG. 5D. The processing is described in detail as follows.

In order to make the explanation simple, only a portion of the waveform of FIG. 5B output by the detector 11 between sampling points d1 and d10 is described. First of all, at a first step, each sampling point which corresponds to a scanning position is evaluated by finding output deviations between the sampling point and the immediately preceding and succeeding sampling points and comparing the output deviations with a fixed value z.

To put it more concretely, first of all, let attention be paid to a sampling point d2 between the sampling point d1 and a sampling point d3. As shown in the figure, since relations $|d2-d1|<z$ and $|d2-d1|<z$ hold true, where notation dn (n=1 to 3) in the relations represents an output at the sampling point dn, the output at the sampling point d2 is not deleted. By the same token, let the attention this time be paid to a sampling point d3 between the sampling point d2 and a sampling point d4. As shown in the figure, since relations $|d3-d2|<z$ and $|d3-d4|>z$ hold true, the output at the sampling point d3 is not deleted. Further, let the attention be paid to a sampling point d4 between the sampling point d3 and a sampling point d5. As shown in the figure, since relations $|d4-d3|>z$ and $|d4-d5|>z$ hold true, indicating that the output deviations of the sampling point d4 from both the sampling points d3 and d5 is greater than the fixed value z, the output at the sampling point d4 is deleted.

Figure 5C:
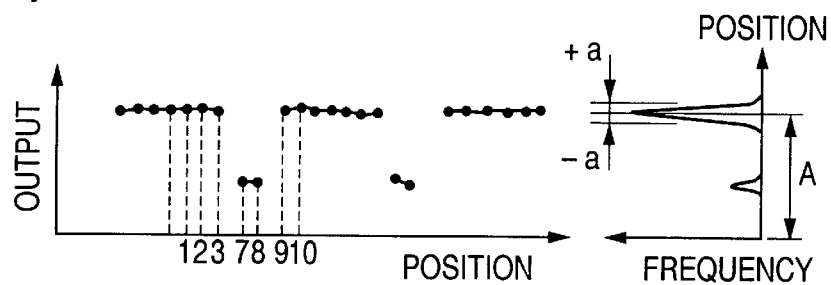
Figure 5D:
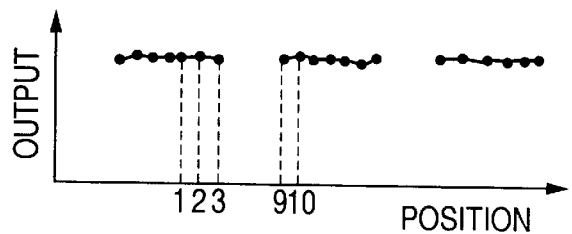
Figure 6:
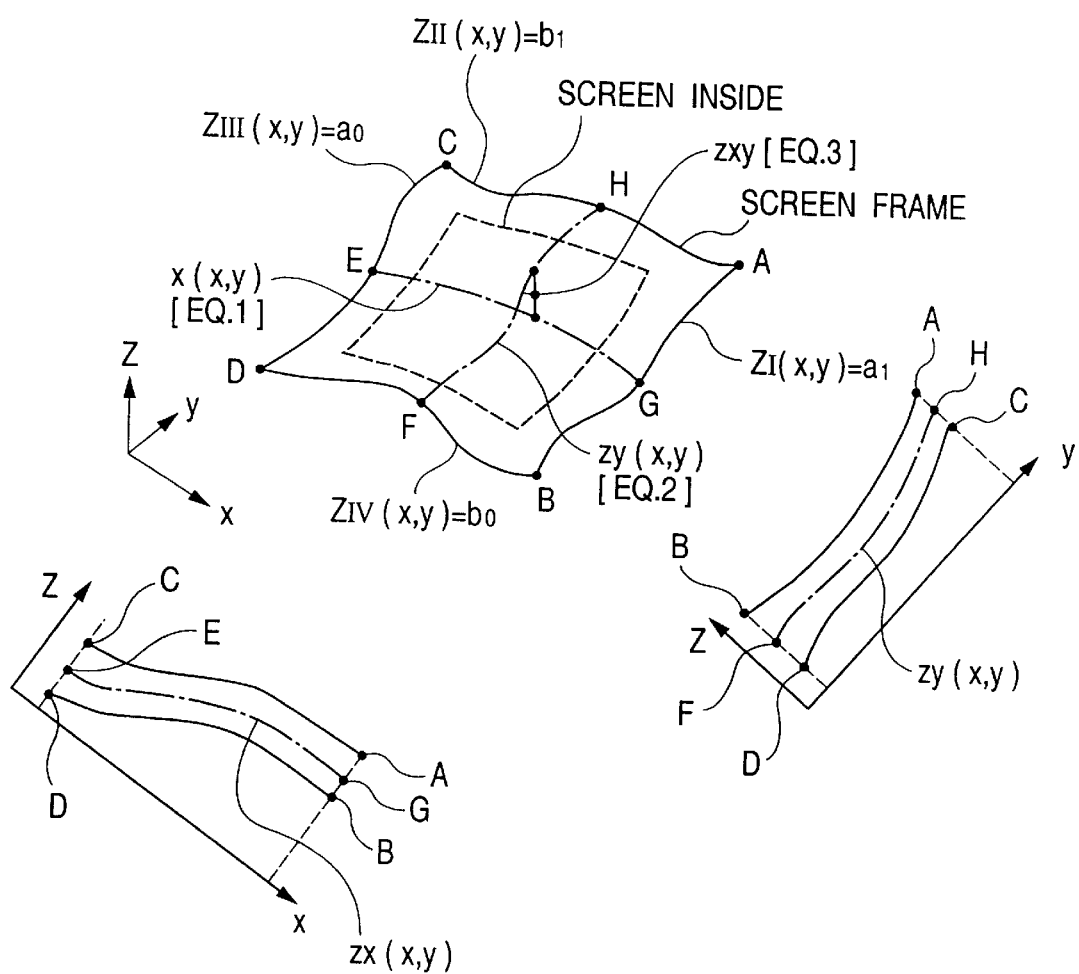
FIG. 6 is a diagram showing a squint view of the surface of a screen, a cross section of the screen seen in the X direction and a cross section of the screen seen in the Y direction.
Figure 7:
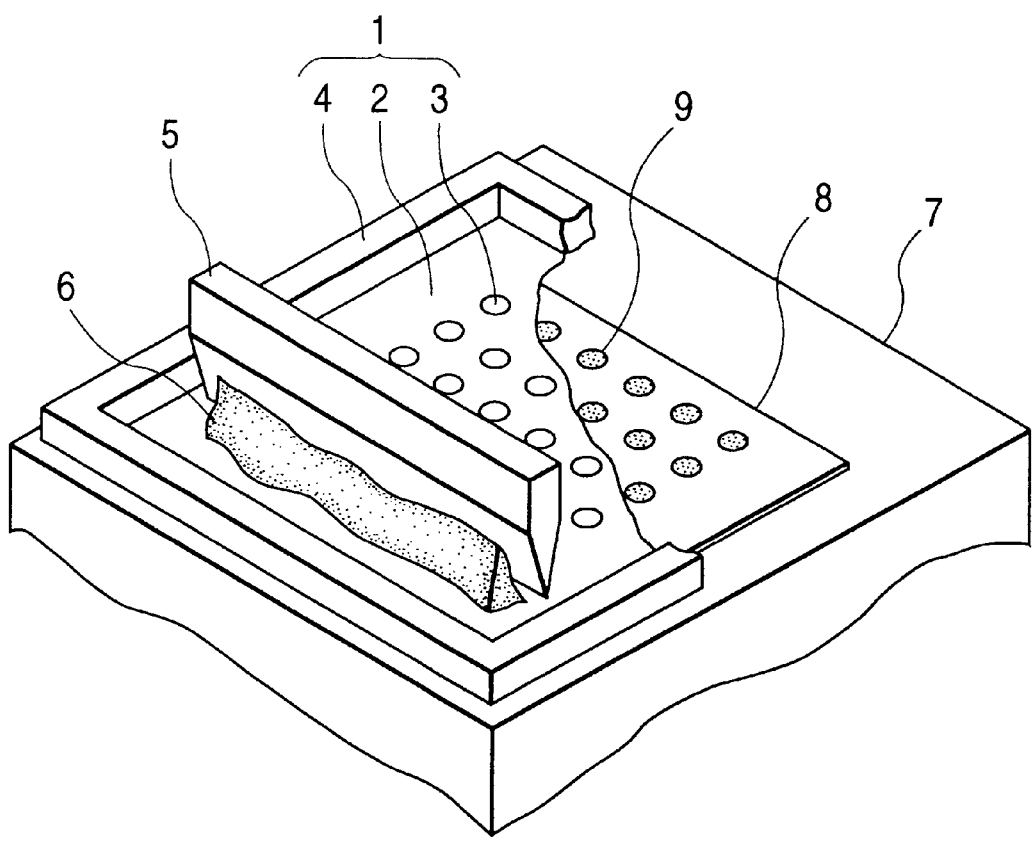
FIG. 7 is a squint-view diagram showing a relation between the screen and a squeegee of an ordinary screen printer.

The processing described above is repeated for sampling points following the sampling point d4. Results of the processing described above for the sampling points between d1 and d10 are shown in FIG. 5C. As shown in the figure, the outputs at the sampling points d1, d2, d3, d9 and d10 are not deleted.

Then, at a second step following the first step, a histogram showing an output frequency distribution is found for the results of processing obtained at the first step and shown on the right side of FIG. 5C. Let notations A and a shown in the histogram each denote an adjustable value of the output. If only outputs at the sampling points in the range A±a are extracted, the results of processing are reduced to that shown in FIG. 5D wherein only outputs at the sampling points d7 and d8 are eliminated from the result shown in FIG. 5C. As a result, only outputs at the sampling points d1, d2, d3, d9 and d10 are eventually extracted as data to form the shape of the surface.

Thus, in such a hole-noise removing process, outputs at a pattern hole 3 and sampling points in close proximity to the pattern hole 3 are deleted efficiently no matter how randomly the pattern holes 3 are formed on the surface 1A of the screen 1 and no matter how much the scanning direction is inclined from the orientation parallel to the direction in which the pattern holes 3 are formed on the surface 1A of the screen 1. As a result, the shape of the surface can be extracted pretty well regardless of what size and what form each of the pattern holes 3 has.

Next, the processing carried out by the internal-surface-shape inferring unit 203 is explained. In the screen 1, the rigidity of the circumference surface on the external frame 4 is better in comparison with that of the inner surface 4 formed by each pattern hole 3. The inventor of the present invention has discovered from experiments the fact that the detection of the shape of the internal surface follows the shape and deformation of the circumference surface of the external frame 4. That is to say, if absolute height displacement data of the external frame 4 can be found by scanning the circumference surface of the external frame 4, a reference surface shape of the inner surface can also be inferred with ease. A method for inferring the reference surface shape is explained by referring to FIG. 6 in concrete terms as follows.

In order to make the explanation simple, let the four corners (vertexes) of the external frame 4 be denoted by notations A to D and let the height data (absolute height displacement data) on the segment AB obtained by actual scanning be Zi. Likewise, let the absolute height displacement data on the segments AC, CD and BD be Zii, Ziii and Ziv respectively. The surface-shape data zx(x, y) on an zx-plane cross section shown in FIG. 6 can be extracted from the height data Zii and Ziv and the surface-shape data zy(x, y) on a zy-plane cross section also shown in the figure can be extracted from the height data Zi and Ziii wherein notations x, y and z are axes of the three-dimensional space. A reference surface shape of the screen in the entire xyz space can be extracted from the extracted height data zx(x, y) and zy(x, y) on these cross sections. The height xyz(x, y) of each xy point at x and y coordinates of the initial reference surface shape is computed as an average of the height zx(x, y) on the zx-plane cross section passing through the xy point and the height zy(x, y) of on the zy-plane cross section passing through the xy point.

The computed height of xy point is then compared with the height data Zi, Zii, Ziii and Ziv of the segments AB, AC, CD and BD respectively in the xyz space. Differences between the computed height of each xy point and the heights Zi, Zii, Ziii and Ziv of the segments AB, AC, CD and BD found equal to or smaller than a predetermined value indicate that the xy point is indeed a point of the reference surface shape being inferred. If the differences between the height of each xy point and the heights Zi, Zii, Ziii and Ziv of the segments AB, AC, CD and BD are found greater than a predetermined value, the above processing based on the immediately preceding inferred reference surface shape is repeated till the differences between each xy point and the immediately preceding inferred reference surface shape are found smaller than the predetermined value.

To put it concretely, a reference surface shape $z(x, y)$ described above is inferred by adopting an inference method based on the following formulas. It should be noted that the equality symbol '=' in the formulas means substitution of an expression on the right-hand side of the equality symbol for a quantity on the left-hand side of the equal symbol. The method begins with a first step at which the reference surface shape $z(x, y)$ is initialized ($z(x, y)=0$) for all points $(x, y)$ on the horizontal xy plane. Then, at a second step, an initial reference surface shape within the frame 4 is inferred by using the height data Zi, Zii, Ziii and Ziv, measured height data of the frame 4 of the screen 1 as described above. First of all, the surface-shape data $zx(x, y)$ on the zx-plane cross sections is found by interpolation of the height data $Zii(x, y)$ and $Ziv(x, y)$ as follows:

$$zx(x, y)=\{(y-b0)/(b1-b0)\}\{Zii(x, b1)-Ziv(x, b0)\}+Ziv(x, b0) \quad (1)$$

where $Zii(x, y)$ and $Ziv(x, y)$ are measured height data in the x direction.

By the same token, the surface-shape data $zy(x, y)$ on the zy-plane cross sections is found by interpolation of the height data $Zi(x, y)$ and $Ziii(x, y)$ as follows:

$$zy(x, y)=\{(y-a0)/(a1-a0)\}\{Zi(a1, y)-Ziii(a0, y)\}+Ziii(a0, y) \quad (2)$$

where $Zi(x, y)$ and $Ziii(x, y)$ are measured height data in the y direction.

Height data xyz $(x, y)$ is then found as an average of $zx(x, y)$ and $zy(x, y)$ calculated by using Eqs. 1 and 2 respectively as follows:

$$zxy(x, y)=\{zx(x, y)+zy(x, y)\}/2 \quad (3)$$

Subsequently, at a third step, the reference surface shape $z(x, y)$ within the frame 4 is updated as follows:

$$z(x, y)=z(x, y)+zxy(x, y) \quad (4)$$

Then, at a fourth step, errors in inferred reference surface shape are found as differences between the reference surface shape $z(x, y)$ calculated by Eq. 4 and the measured height data Zi to Ziv as follows:

$$Zi(a1, y)=Zi(a1, y)-z(a1, y) \quad (5)$$

$$Zii(x, b1)=Zii(x, b1)-z(x, b1) \quad (6)$$

$$Ziii(a0, y)=Ziii(a0, y)-z(a0, y) \quad (7)$$

$$Ziv(x, b0)=Ziv(x, b0)-z(x, b0) \quad (8)$$

If the errors are found equal to or smaller than a predetermined value, then a fifth step is executed. Otherwise, processing is repeated starting with the second step for finding a better reference surface shape z $(x, y)$. At the fifth step, the amount of unevenness, that is, the displacements of the inferred reference height data z $(x, y)$ of Eq. 4, is calculated as differences between the inferred reference surface shape $z(x, y)$ and actually measured data on the surface of the screen 1 for an external frame 4 planted forcibly to form a flat plane as follows:

$$Ei(x, y)=Zi(x, y)-z(x, y) \quad (9)$$

where

Ei(x, y): the amount of unevenness,

Zi (x, y): actually measured data on the screen surface, z(x, y): the reference surface shape found at the third step and d: a level difference between the external frame and the screen, a design value.

As described above, a reference surface shape can be inferred from an actually measured shape of the external frame in a recursive process so that the errors between the inferred surface shape and the actually measured shape of the external frame are minimized. As a result, even if an inner surface of the screen is deformed following the external frame 4, the local unevenness deformation can be extracted with a high degree of accuracy. In the case of a plane member with pattern holes formed on the surface thereof such as a screen, information on locations of the pattern holes can be obtained from design data or from results produced by the hole-noise removing processing in advance so that only local surface-shape defects can be detected.

What has been described above is an embodiment wherein a plane member employed therein is relatively rigid so that deformation of the surface thereof follows deformation of a member having good rigidity provided on the circumference of the plane member. The following is description of an embodiment wherein a plane member employed therein is less rigid than a member provided on the circumference of the plane member so that deformation of the surface of the plane member hardly follows deformation of the member having good rigidity on the circumference. These embodiment is explained by referring to FIGS. 8 to 10. In the case of the embodiment shown in FIG. 8, pieces of processing from the measurement of the absolute height displacement data to the supplying of the data to the microcomputer 30 are the same as the embodiment shown in FIG. 1. For this reason, elements shown in FIG. 8 identical with those of FIG. 1 are denoted by the same reference numerals used for denoting the latter.

As shown in the figure, the microcomputer 30 comprises a hole/noise removing unit 301, a surface-shape extracting unit 302, a rough-surface-shape inferring unit 303, an (extracted value–inferred value) computing unit 304 and a comparator 305. First of all, the hole/noise removing unit 301 removes noise generated by pattern holes 3 and areas surrounding them from the absolute height displacement data at the corresponding scanning locations in accordance with the absolute height displacement data itself which is obtained sequentially from the detector 11. Then, the surface-shape extracting unit 302 extracts the shape of the surface 1A excluding the pattern holes 3 on the basis of the absolute height displacement data at the corresponding scanning locations on the surface 1A. In the mean time, while the shape of the surface 1A is being extracted, the rough-surface-shape inferring unit 303 infers a reference surface shape for the surface 1A on the screen 1 by extracted rough curved-surface approximation.

The (extracted value–inferred value) computing unit 304 then computes a difference between the shape of the surface 1A extracted by the surface-shape extracting unit 302 and the reference surface shape for the surface 1A inferred by the internal-surface-shape inferring unit 303, supplying the difference to the comparator 305 which compares the difference with a predetermined allowable value. A difference found greater than the allowable value indicates that a local surface-shape defect exists on the surface 1A at position coordinates (X, Y). In this case, the stage controller 21 moves the marking unit 12 to the location of the surface-shape defect at the coordinates (X, Y) by driving the X stage 16 and the Y stage 13. The location is then marked with something that allows the surface-shape defect to be seen with ease.

The following is description of the hole-noise removing process carried out by the hole-noise removing unit 301 with reference to FIG. 9. This embodiment adopts a method for removing hole data and noise different from that embraced by the hole-noise removing unit 201 shown in FIG. 1 which has been explained by referring to FIG. 5. In the case of the present embodiment, a noise component with a large output is removed from a histogram spread over a wide area and then an infinitesimal noise component is eliminated from a small histogram as shown in FIG. 9.

Figure 9A:
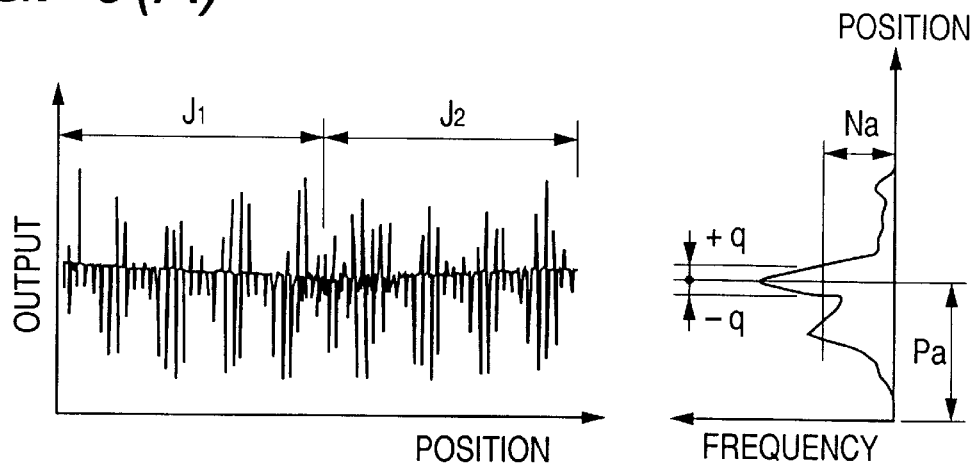
FIGS. 9(A)–9(C) are diagrams each showing a relation between the detection position and the output in a hole-noise removing unit in the second embodiment of the present invention.

Corresponding to FIG. 5B, FIG. 9A shows a relation between the position and the output of the sensor which contains noise components. First of all, a large histogram for regions J1 and J2 are found. From this large histogram, a small histogram representing frequencies higher than a predetermined value Na is extracted and an output Pa with a peak frequency is identified. Then, an adjustable constant q is determined so that the selected small histogram covers only outputs in the range Pa±q. This is because it is desirable to extract the most protruding portion of the large histogram excluding noise with a high degree of fidelity.

Figure 9B:
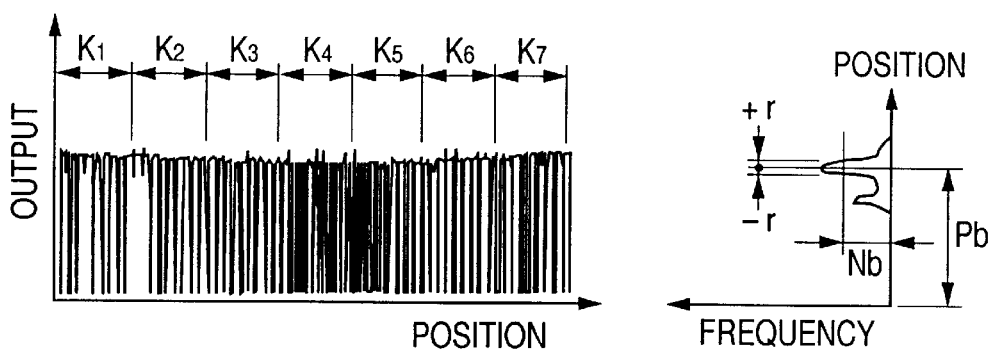
Figure 9C:
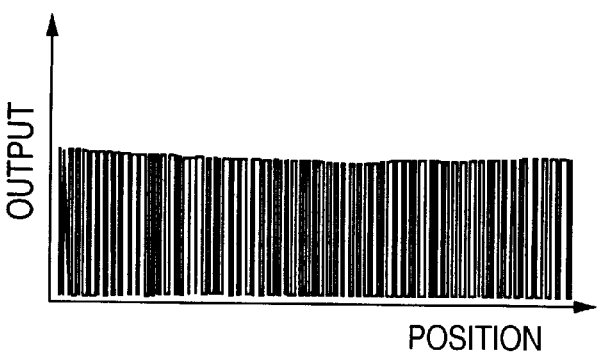

FIG. 9B shows a waveform found by the processing of the large histogram covering a wide area described above. The waveform shown in FIG. 9B is then divided into small portions covering small areas. In the example shown in the figure, the waveform is divided into seven portions. A histogram shown on the right side of FIG. 9B covers a first portion K1. From this histogram, a small histogram representing frequencies higher than a predetermined value Nb is extracted and an output Pb with a peak frequency is identified. Then, an adjustable constant r is determined so that the selected small histogram covers only outputs in the range Pb±r. FIG. 9C shows a waveform found by the processing of the histogram covering the portion K1 described above. This method has an effect that the shape of the surface can be extracted with a high fidelity by excluding spike noise even if waviness exists in the shape of the surface.

Figure 10A:
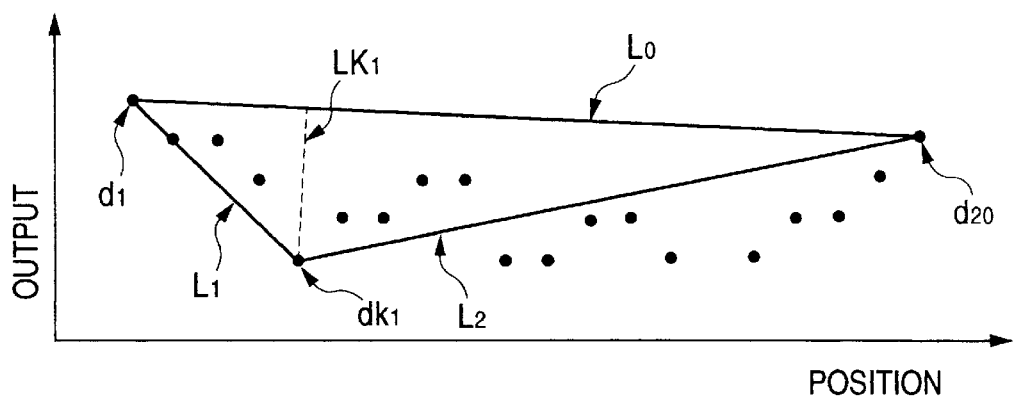
FIGS. 10(A)–10(B) are diagrams each showing a relation between the detection position and the output in an inner-surface-shape inferring unit employed in the second embodiment of the present invention.
Figure 10B:
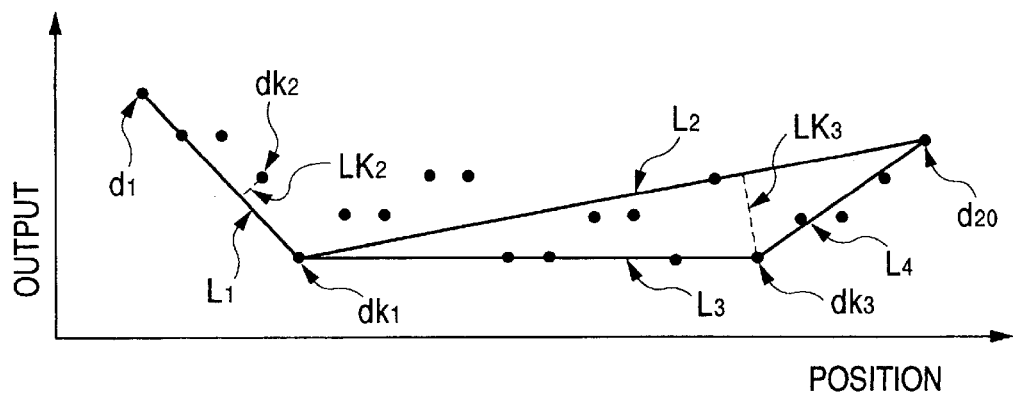

The following is description of a polygonal-line fitting technique adopted by the surface-shape extracting unit 302 and the rough-surface-shape inferring unit 303 by referring to FIGS. 10A and 10B. The polygonal-line fitting technique is applied to sampling points obtained as an output waveform shown in FIG. 5D or 9C. Let sampling points be denoted by notations d1 to dn where notation n is the number of sampling points. The polygonal-line fitting technique shown in FIG. 10 is implemented for n=20. Sampling points d0 to d20 shown in FIG. 10A are arranged in the order sampling points shown in FIGS. 5B and 9C are scanned.

This sequence of sampling points are approximated by straight lines in accordance with a procedure described below. First of all, the sampling point d1 is connected to the sampling point d20 by a straight line L0. Then, distances from the straight line L0 to the sampling points between d1 and d20 are found. A sampling point with a longest distance is identified. Let the sampling point and the longest distance thereof be denoted by notations dk1 and Lk1 respectively. The longest distance Lk1 is compared with a predetermined value Lth. If the longest distance Lk1 is found longer than the value Lth, the straight line L0 is replaced by a straight line L1 connecting the sampling point d1 to the sampling point dk1 and a straight line L2 connecting the sampling point dk1 to the sampling point d20.

The operation carried out on the straight line L0 described above is performed on the straight lines L1 and L2. To be more specific, a point dk2 with a longest distance Lk2 from the straight line L1 and a point dk3 with a longest distance Lk3 from the straight line L2 are found as shown in FIG. 10B. Likewise, the longest distances Lk2 and Lk3 are compared with the predetermined value Lth. If Lk2<Lth and Lk3>Lth, the straight line L1 is taken as an approximation segment. On the other hand, the straight line L2 is replaced by a straight line L3 connecting the sampling point dk1 to the sampling point dk3 and a straight line L4 connecting the sampling point dk3 to the sampling point dk20. Then, the operation carried out on the straight lines L1 and L2 is now performed on the straight lines L3 and L4. The operation described above is repeated recursively till final approximation segments are determined. If a point exists between two points connected by an approximation segment after the final approximation segments have been determined, the distance from the point to the approximation segment must be shorter than the predetermined value Lth.

As a result, the sampling points d1 is connected to the sampling point d20 by an approximating polygonal line with all the given sampling points located within distances from the polygonal line shorter then the predetermined value Lth. If the value Lth is set at 0, the polygonal line resulting from the application of the polygonal-line fitting technique will be a polygonal line passing through all the sampling points. Thus, by setting Lth at a small value, local unevenness of a series of sampling points can be actualized by an approximating polygonal line. If Lth is set at a large value, on the other hand, local unevenness of a series of sampling points will be ignored, allowing only big waviness or big unevenness of the series of sampling points to be actualized. The value Lth for extracting big unevenness is set on the basis of a deformation quantity which can be adjusted when the object of examination is actually used. On the other hand, the value Lth for extracting local unevenness is set on the basis of the deformation quantity of a defect to be actualized.

Thereafter, let notation S(t) represent an approximating polygonal line for actualizing big unevenness while notation R(t) represent an approximating polygonal line for actualizing local unevenness where notation t denotes the position on the scanning direction.

The surface-shape extracting unit 302 generates an approximating polygonal line R(t) actualizing local unevenness while the rough-shape extracting unit 303 generates an approximating polygonal line S(t) actualizing big unevenness. The (extracted value–inferred value) computing unit 304 computes the difference between the two approximating polygonal lines |S(t)–R(t)| or |R(t)–S(t)|. The comparator 305 compares the difference with a predetermined allowable value. While polygonal-line fitting in the scanning direction has been described so far, it is obvious that the polygonal-line-fitting technique can be applied to a direction perpendicular to the scanning direction by carrying out the same processing. Thus, with this technique, it is possible to extract local unevenness of a two-dimensional surface.

Figure 11:
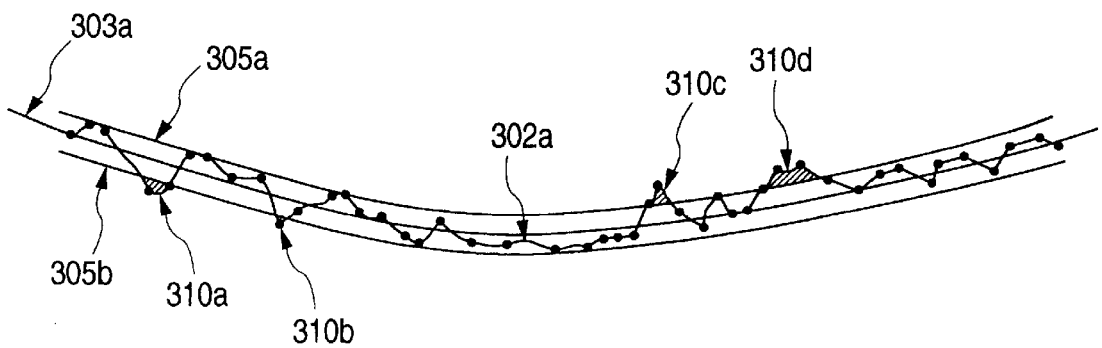
FIG. 11 is a diagrams showing a relation between the detection position and the output in an unevenness extracting process of the second embodiment of the present invention.

FIG. 11 is a diagram showing the process to detect unevenness carried out by the comparator 305. Reference numeral 302a shown in the figure is the output of the surface-shape extracting unit 302 and reference numeral 303a denotes the output of the rough-shape extracting unit 303. Reference numerals 305a and 305b are predetermined allowable values used for comparison by the comparator 305. Locations of unevenness 310a, 310b, 310c and 310d where the difference between the outputs 302a and 302b exceeds the predetermined allowable value 305a or 305b are each output as a defect.

In order to treat surface shapes of an object with a higher degree of fidelity, a curve-fitting technique can be introduced. A typical curve-fitting technique is described in Paragraph 3.3 'Third-order Interpolation' of a reference with a title "Numerical recipes in C," authored by W. H. Press, a publication of Technology Review Corporation. According to this technique, a spline curve or the like can be used as a rough curve interpolating vertexes including end points of S(t) representing big unevenness. According to a technique described in Paragraph 3.1 'Interpolation and Extrapolation Using Polynomials' of the same reference with a title "Numerical recipes in C," authored by W. H. Press, a publication of Technology Review Corporation, a curve is applied to vertexes including end points with the order of the curve set at a value equal the number of vertexes minus one. According to a technique described in a reference authored by P. Saint-Marc, et al. with a title "B-Spline Contour Representation and Symmetry Detection," IEEE Trans, PAMI, Vol. 15 No. 11, pp 1191 to 1197, November 1993, the number of vertexes including end points is treated as a control-point count. A spline curve provided by using this technique can be applied to sampling points output by the hole-noise removing unit 301. The techniques described above can also be adopted to generate a local curve. Let the resulting rough and local curves be C(t) and c(t) respectively. In this case, the difference computed by the (extracted value−inferred value) computing unit 304 can be found as $|C(t)-c(t)|$ or $(C(t)-c(t))$.

It should be noted that, while the present invention has been explained by taking a mask mainly used as a screen as an example, the description is not to be construed in a limiting sense. That is to say, the present invention can also be applied to evaluation of deformation of a rigid sheet material such as a steel plate. In particular, the present invention is effective for inspection of the surface of a member with holes bored through it such as a punching metal. Additional fields of application include deformation evaluation and shape measurement of the surface of a steel plate such as a separator used for example in a fuel battery. The present invention is readily applicable as it is to such an application.

As described above, according to the present invention, a local shape defect of an inner surface of an ordinary plane member with a configuration having a member with good rigidity provided on the circumference thereof and holes bored through the inner surface can be detected as a state distinguished from a big waviness deformation with a high degree of accuracy without the need to scan the holes.

In addition, according to the present invention, a local shape defect of an inner surface of an ordinary plane member with a configuration having a member with good rigidity provided on the circumference thereof and holes bored through the inner surface can be detected as a state distinguished from a big waviness deformation with a high degree of accuracy and without being affected by the holes.

On the top of that, according to the present invention, a local shape defect of an inner surface of an ordinary plane member with a configuration having at least a member with good rigidity provided on the circumference thereof and with or without holes bored through the inner surface can be detected as a marked state distinguished from a big waviness deformation with a high degree of accuracy, with a high degree of accuracy and without being affected by the holes.

Furthermore, according to the present invention, a local shape defect of an inner surface of an ordinary plane member with a configuration having a member with good rigidity provided on the circumference thereof can be detected as a state distinguished from a big waviness deformation with a high degree of accuracy.

In addition, according to the present invention, a local shape defect of an inner surface of an ordinary plane member with a configuration having a member with good rigidity provided on the circumference thereof and holes bored through the inner surface can be detected as a state distinguished from a big waviness deformation with a high degree of accuracy without the need to scan the holes.

On the top of that, according to the present invention, a local shape defect of an inner surface of an ordinary plane member with a configuration having a member with good rigidity provided on the circumference thereof and holes bored through the inner surface can be detected as a state distinguished from a big waviness deformation with a high degree of accuracy without the need to scan the holes.

Furthermore, according to the present invention, a local shape defect of an inner surface of an ordinary plane member with a configuration having at least a member with good rigidity provided on the circumference thereof and with or without holes bored through the inner surface can be detected as a marked state distinguished from a big waviness deformation with a high degree of accuracy, with a high degree of accuracy and without being affected by the holes.

In addition, according to the present invention, a local shape defect of an inner surface of an ordinary plane member with a configuration having holes bored through the inner surface can be detected as a state distinguished from a big waviness deformation with a high degree of accuracy.

What is claimed is:

1. A surface-shape-defect inspecting method for identifying a shape defect of a first plane member having a low rigidity which is connected with a second plane member having a high rigidity greater than the low rigidity of said first plane member, said method comprising the steps of:

scanning optically the entire area of said first and second plane members;

extracting a surface shape of said first and second plane members as absolute height displacement data at scanning positions;

finding a difference between a rough reference surface shape for the surface of said first plane member inferred from said surface shape of said second plane member and said surface shape of said first plane member, and using said difference as relative height displacement data with respect to said rough reference surface shape; and detecting said shape defect on the surface of said first plane member by identifying the location of said shape defect through comparison of said relative height displacement data with predetermined allowable displacement data.

2. A surface-shape-defect inspecting apparatus for identifying a shape defect of a first plane member having a low rigidity which is connected with a second plane member having a high rigidity greater than the low rigidity of said first plane member, said apparatus comprising at least:

an absolute-height-displacement extracting means for scanning optically the entire area of said first and second plane members to extract a surface shape of said first and second plane members as absolute height displacement data at scanning positions;

a reference-surface-shape inferring means for inferring a rough reference surface shape for the surface of said first plane member from said surface shape of said second plane member;

a relative-height-displacement extracting means for finding a difference between said rough reference surface shape inferred by said reference-surface-shape inferring means and said surface shape of said first plane member output by said absolute-height-displacement extracting means, and using said difference as relative height displacement data with respect to said rough reference surface shape; and a shape-defect detecting means for defecting said shape defect on the surface of said first plane member by identifying the location of said shape defect through comparison of said relative height displacement data with predetermined allowable displacement data.

3. A surface-shape-defect inspecting method for identifying a shape defect on the surface of a plane member with holes bored through said surface, said method comprising the steps of:

scanning optically the entire area of said plane member while excluding said holes in accordance with design data;

extracting a surface shape of said plane member as absolute height displacement data at scanning positions which exclude said holes;

finding a difference between a rough reference surface shape for the surface of said plane member inferred from said surface shape of said plane member and said surface shape of said plane member, and using said difference as relative height displacement data with respect to said rough reference surface shape; and detecting said shape defect on the surface of said plane member by identifying the location of said shape defect through comparison of said relative height displacement data with predetermined allowable displacement data.

4. A surface-shape-defect inspecting apparatus for identifying a shape defect on the surface of a plane member with holes bored through said surface, said apparatus comprising at least:

an absolute-height-displacement extracting means for scanning optically the entire area of said plane member while excluding said holes in accordance with design data to extract a surface shape of said plane member as absolute height displacement data at scanning positions excluding said holes;

a reference-surface-shape inferring means for inferring a rough reference surface shape for the surface of said plane member from said surface shape of said plane member;

a relative-height-displacement extracting means for finding a difference between said rough reference surface shape inferred by said reference-surface-shape inferring means and an inner-surface shape of said plane member output by said absolute-height-displacement extracting means, and using said difference as relative height displacement data with respect to said rough reference surface shape; and a shape-defect detecting means for defecting said shape defect on said inner surface of said plane member by identifying the location of said shape defect through comparison of said relative height displacement data with predetermined allowable displacement data.

5. A surface-shape-defect inspecting method for identifying a shape defect on the surface of a plane member with holes bored through said surface, said method comprising the steps of:

scanning optically the entire area of said plane member;

extracting a surface shape of said plane member as absolute height displacement data at scanning positions in said entire area by treating said holes as undetectable regions or masked regions in accordance with design data;

finding a difference between a rough reference surface shape for the surface of said plane member inferred from said surface shape of said plane member and said surface shape of said plane member, and using said difference as relative height displacement data with respect to said rough reference surface shape; and detecting said shape defect on the surface of said plane member by identifying the location of said shape defect through comparison of said relative height displacement data with predetermined allowable displacement data.

6. A surface-shape-defect inspecting apparatus for identifying a shape defect on the surface of a plane member with holes bored through said surface, said apparatus comprising at least:

an absolute-height-displacement extracting means for scanning optically the entire area of said plane member by treating said holes as undetectable regions or masked regions in accordance with design data to extract a surface shape of said plane member as absolute height displacement data at scanning positions;

a reference-surface-shape inferring means for inferring a rough reference surface shape for the surface of said plane member from said surface shape of said plane member;

a relative-height-displacement extracting means for finding a difference between said rough reference surface shape inferred by said reference-surface-shape inferring means and an inner-surface shape of said plane member output by said absolute-height-displacement extracting means, and using said difference as relative height displacement data with respect to said rough reference surface shape; and a shape-defect detecting means for detecting said shape defect on said inner surface of said plane member by identifying the location of said shape defect through comparison of said relative height displacement data with predetermined allowable displacement data.

7. A surface-shape-defect inspecting method for identifying a shape defect on the surface of a plane member with holes bored through said surface, said method comprising the steps of:

scanning optically the entire area of said plane member;

extracting a surface shape of an area excluding said holes of said plane member as absolute height displacement data at scanning positions;

finding a difference between a rough reference surface shape for the surface of said plane member inferred from said surface shape of said plane member and said surface shape of said plane member, and using said difference as relative height displacement data with respect to said rough reference surface shape; and detecting said shape defect on the surface of said plane member by identifying the location of said shape defect through comparison of said relative height displacement data with predetermined allowable displacement data.

8. A surface-shape-defect inspecting method for identifying a shape defect on the surface of a plane member with holes bored through said surface, said method comprising the steps of:

scanning optically the entire area of said plane member;

extracting a surface shape of an area excluding said holes of said plane member as absolute height displacement data at scanning positions by carrying out processing to eliminate noise and hole portions of absolute height displacement data of a plurality of consecutive scanning positions;

finding a difference between a rough reference surface shape inferred from said surface shape of said plane member and said surface shape of said plane member, and using said difference as relative height displacement data with respect to said rough reference surface shape; and detecting said shape defect on said inner surface of said plane member by identifying the location of said shape defect through comparison of said relative height displacement data with predetermined allowable displacement data.

9. A surface-shape-defect inspecting apparatus for identifying a shape defect on an inner surface of a plane member with holes bored through said surface, said apparatus comprising at least:

an absolute-height-displacement extracting means for scanning optically the entire area of said plane member to extract a surface shape of said plane member excluding said holes as absolute height displacement data at scanning positions;

a reference-surface-shape inferring means for inferring a rough reference surface shape for the surface of said plane member from said surface shape of said plane member;

a relative-height-displacement extracting means for finding a difference between said rough reference surface shape inferred by said reference-surface-shape inferring means and an inner-surface shape of said plane member output by said absolute-height-displacement extracting means, and using said difference as relative height displacement data with respect to said rough reference surface shape; and a shape-defect detecting means for detecting said shape defect on said inner surface of said plane member by identifying the location of said shape defect through comparison of said relative height displacement data with predetermined allowable displacement data.

10. A surface-shape-defect inspecting method for identifying a shape defect on the surface of a plane member without regard to whether or not holes are bored through said surface, said method comprising the steps of:

scanning optically the entire area of said plane member;

extracting a surface shape of an area excluding said holes of said plane member as absolute height displacement data at scanning positions;

finding a difference between a rough reference surface shape for the surface of said plane member inferred from said surface shape of said plane member and said surface shape of said plane member, and using said difference as relative height displacement data with respect to said rough reference surface shape; and detecting said shape defect by identifying the location of said shape defect through comparison of said relative height displacement data with predetermined allowable displacement data while marking the location of said shape defect on said inner surface of said plane member.

11. A surface-shape-defect inspecting apparatus for identifying a shape defect on the surface of a plane member without regard to whether or not holes are bored through said surface, said apparatus comprising at least:

an absolute-height-displacement extracting means for scanning optically the entire area of said plane member to extract a surface shape of said plane member while excluding said holes as absolute height displacement data at scanning positions;

a reference-surface-shape inferring means for inferring a rough reference surface shape for the surface of said plane member from said surface shape of said plane member;

a relative-height-displacement extracting means for finding a difference between said rough reference surface shape inferred by said reference-surface-shape inferring means and an inner-surface shape of said plane member output by said absolute-height-displacement extracting means, and using said difference as relative height displacement data with respect to said rough reference surface shape;

a shape-defect detecting means for detecting said shape defect on said inner surface of said plane member by identifying the location of said shape defect through comparison of said relative height displacement data with predetermined allowable displacement data; and a marking means for marking said location of said shape defect on said inner surface of said plane member identified by said shape-defect detecting means.

12. A surface-shape-defect inspecting method for identifying a shape defect on an inner surface of a plane member with a configuration including a member having good rigidity provided on the circumference of said plane member which has a rigidity different from the good rigidity, said method comprising the steps of:

scanning optically the entire area of said plane member;

extracting an inner-surface shape of said plane member as absolute height displacement data at scanning positions;

finding a difference between a reference surface shape inferred from a circumference-surface shape of said member having good rigidity and said inner-surface shape of said plane member, and using said difference as relative height displacement data with respect to said reference surface shape; and detecting said shape defect on said inner surface by identifying the location of said shape defect through comparison of said relative height displacement data with predetermined allowable displacement data.

13. A surface-shape-defect inspecting method for identifying a shape defect on an inner surface of a plane member with a configuration including a member having good rigidity provided on the circumference of said plane member which has a rigidity different from the good rigidity, said method comprising the steps of:

scanning optically the entire area of said plane member;

extracting an inner-surface shape of said plane member as absolute height displacement data at scanning positions;

finding a difference between a reference surface shape inferred from a circumference-surface shape of said member having good rigidity provided on four sides of said circumference and said inner-surface shape of said plane member, and using said difference as relative height displacement data with respect to said reference surface shape; and detecting said shape defect on said inner surface by identifying the location of said shape defect through comparison of said relative height displacement data with predetermined allowable displacement data.

14. A surface-shape-defect inspecting apparatus for identifying a shape defect on an inner surface of a plane member with a configuration including a member having good rigidity provided on the circumference of said plane member which has a rigidity different from the good rigidity, said apparatus comprising at least:

an absolute-height-displacement extracting means for scanning optically the entire area of said plane member to extract an inner-surface shape of said plane member as absolute height displacement data at scanning positions;

a reference-surface-shape inferring means for inferring a reference surface shape for said inner surface of said plane member from a circumference-surface shape of said member having good rigidity provided on said circumference;

a relative-height-displacement extracting means for finding a difference between said reference surface shape inferred by said reference-surface-shape inferring means and said inner-surface shape of said plane member output by said absolute-height-displacement extracting means, and using said difference as relative height displacement data with respect to said reference surface shape; and a shape-defect detecting means for defecting said shape defect on said inner surface of said plane member by identifying the location of said shape defect through comparison of said relative height displacement data with predetermined allowable displacement data.

15. A surface-shape-defect inspecting method for identifying a shape defect on an inner surface of a plane member with a configuration including a member having good rigidity provided on the circumference of said plane member and holes bored through said inner surface, said method comprising the steps of:

scanning optically the entire area of said plane member excluding said holes in accordance with design data;

extracting an inner-surface shape of said plane member as absolute height displacement data at scanning positions;

finding a difference between a reference surface shape inferred from a circumference-surface shape of said member having good rigidity and said inner-surface shape of said plane member, and using said difference as relative height displacement data with respect to said reference surface shape; and detecting said shape defect on said inner surface by identifying the location of said shape defect through comparison of said relative height displacement data with predetermined allowable displacement data.

16. A surface-shape-defect inspecting apparatus for identifying a shape defect on an inner surface of a plane member with a configuration including a member having good rigidity provided on the circumference of said plane member and holes bored through said inner surface, said apparatus comprising at least:

an absolute-height-displacement extracting means for scanning optically the entire area of said plane member excluding said holes in accordance with design data to extract an inner-surface shape of said plane member as absolute height displacement data at scanning positions;

a reference-surface-shape inferring means for inferring a reference surface shape for said inner surface of said plane member from a circumference-surface shape of said member having good rigidity provided on said circumference;

a relative-height-displacement extracting means for finding a difference between said reference surface shape inferred by said reference-surface-shape inferring means and said inner-surface shape of said plane member output by said absolute-height-displacement extracting means, and using said difference as relative height displacement data with respect to said reference surface shape; and a shape-defect detecting means for defecting said shape defect on said inner surface of said plane member by identifying the location of said shape defect through comparison of said relative height displacement data with predetermined allowable displacement data.

17. A surface-shape-defect inspecting method for identifying a shape defect on an inner surface of a plane member with a configuration including a member having good rigidity provided on the circumference of said plane member and holes bored through said inner surface, said method comprising the steps of:

scanning optically the entire area of said plane member;

extracting an inner-surface shape of said plane member as absolute height displacement data at scanning positions in an area excluding said holes;

finding a difference between a reference surface shape inferred from a circumference-surface shape of said member having good rigidity and said inner-surface shape of said plane member, and using said difference as relative height displacement data with respect to said reference surface shape; and detecting said shape defect on said inner surface by identifying the location of said shape defect through comparison of said relative height displacement with predetermined allowable displacement data.

18. A surface-shape-defect inspecting method for identifying a shape defect on an inner surface of a plane member with a configuration including a member having good rigidity provided on the circumference of said plane member and holes bored through said inner surface, said method comprising the steps of:

scanning optically the entire area of said plane member;

extracting an inner-surface shape of said plane member as absolute height displacement data at scanning positions in an area excluding said holes by carrying out processing to eliminate noise and hole portions of absolute height displacement data of a plurality of consecutive scanning positions;

finding a difference between a reference surface shape inferred from a circumference-surface shape of said member having good rigidity and said inner-surface shape of said plane member, and using said difference as relative height displacement data with respect to said reference surface shape; and detecting said shape defect on said inner surface by identifying the location of said shape defect through comparison of said relative height displacement data with predetermined allowable displacement data.

19. A surface-shape-defect inspecting apparatus for identifying a shape defect on an inner surface of a plane member with a configuration including a member having good rigidity provided on the circumference of said plane member and holes bored through said inner surface, said apparatus comprising at least:

an absolute-height-displacement extracting means for scanning optically the entire area of said plane member to extract an inner-surface shape of said plane member as absolute height displacement data at scanning positions excluding said holes;

a reference-surface-shape inferring means for inferring a reference surface shape for said inner surface of said plane member from a circumference-surface shape of said member having good rigidity provided on said circumference;

a relative-height-displacement extracting means for finding a difference between said reference surface shape inferred specially by said reference-surface-shape inferring means and said inner-surface shape of said plane member output by said absolute-height-displacement extracting means, and using said difference as relative height displacement data with respect to said reference surface shape; and a shape-defect detecting means for defecting said shape defect on said inner surface of said plane member by identifying the location of said shape defect through comparison of said relative height displacement data with predetermined allowable displacement data.

20. A surface-shape-defect inspecting method for identifying a shape defect on an inner surface of a plane member with a configuration including at least a member having good rigidity provided on the circumference of said plane member without regard to whether or not holes are bored through said surface, said method comprising the steps of:

scanning optically the entire area of said plane member;

extracting an inner-surface shape of said plane member as absolute height displacement data at scanning positions in an area excluding said holes;

finding a difference between a reference surface shape inferred from a circumference-surface shape of said member having good rigidity and said inner-surface shape of said plane member, and using said difference as relative height displacement data with respect to said reference surface shape; and detecting said shape defect on said inner surface by identifying the location of said shape defect through comparison of said relative height displacement data with predetermined allowable displacement data while marking the location of said shape defect on said inner surface of said plane member.

21. A surface-shape-defect inspecting apparatus for identifying a shape defect on an inner surface of a plane member with a configuration including at least a member having good rigidity provided on the circumference of said plane member without regard to whether or not holes are bored through said surface, said apparatus comprising at least:

an absolute-height-displacement extracting means for scanning optically the entire area of said plane member to extract an inner-surface shape of said plane member as absolute height displacement data at scanning positions excluding said holes;

a reference-surface-shape inferring means for inferring a reference surface shape for said inner surface of said plane member from a circumference-surface shape of said member having good rigidity provided on said circumference;

a relative-height-displacement extracting means for finding a difference between said reference surface shape inferred by said reference-surface-shape inferring means and said inner-surface shape of said plane member output by said absolute-height-displacement extracting means, and using said difference as relative height displacement data with respect to said reference surface shape;

a shape-defect detecting means for defecting said shape defect on said inner surface of said plane member by identifying the location of said shape defect through comparison of said relative height displacement data with predetermined allowable displacement data; and a marking means for marking said location of said shape defect on said inner surface of said plane member identified by said shape-defect detecting means.

22. A surface-shape-defect inspecting method for identifying a shape defect on an inner surface of a plane member with holes bored through the surface of said plane member according to any one of claims 3, 5, 7, 8, 10, 15, 17, 18 and 20 said method comprising the steps of:

scanning optically the entire area of said plane member by using a light beam with a diameter equal to or smaller than half the size of each of said holes;

extracting an inner-surface shape of said plane member as absolute height displacement data at scanning positions in an area excluding said holes;

finding a difference between a specially inferred reference surface shape and said inner-surface shape of said plane member, and using said difference as relative height displacement data with respect to said reference surface shape; and detecting said shape defect on said inner surface by identifying the location of said shape defect through comparison of said relative height displacement data with predetermined allowable displacement.

23. A surface-shape-defect inspecting method for identifying a shape defect of a first plane member which is at least partially connected to a second plane member, said method comprising the steps of:

illuminating a surface of the first plane member and a surface of the second plane member;

detecting a light reflected from the surface of the first and second plane members by the illuminating;

inferring a reference surface shape of said first plane member from the detected light reflected from the surface of the second plane member;

calculating a surface shape of the first plane member from the detected light reflected from the surface of the first plane member;

comparing the inferred reference surface shape and the calculated surface shape; and determining a surface-shape-defect of the first plane member using the result of the comparing.

24. A surface-shape-defect inspecting method according to claim 23, wherein said first plane member has a lower rigidity than a rigidity of the second plane member.

25. A surface-shape-defect inspecting method according to claim 24, wherein a periphery of said first plane member is rigidly fixed to the second plane member.

26. A surface-shape-defect inspecting method according to claim 23, wherein said first plane member has holes in the surface thereof.

27. A surface-shape-defect inspecting method for identifying a shape defect of a first plane member which at least partially connected to a second plane member, said method comprising the steps of:

- illuminating a surface of the first plane member;
- detecting a light reflected from the surface of the first plane member by the illuminating;
- inferring a reference surface shape of said first plane member from a desired data of a surface of the second plane member;
- calculating a surface shape of the first plane member from the detecting light reflected from the surface of the first plane member;
- comparing the inferred reference surface shape and the calculated surface shape; and
- determining a surface-shape-defect of the first plane member using the result of the comparing.

28. A surface-shape-defect inspecting method according to claim 27, wherein said first plane member has a lower rigidity than a rigidity of the second plane member.

29. A surface-shape-defect inspecting method according to claim 28, wherein a periphery of said first plane member is rigidly fixed to the second plane member.

30. A surface-shape-defect inspecting method according to claim 27, wherein said first plane member has holes in the surface thereof.

31. A surface-shape-defect inspecting apparatus for identifying a shape defect of a first plane member which is at least partially connected to a second plane member, comprising:

- a light source which illuminates a surface of the first plane member and a surface of the second plane member;
- a detector which detects a light reflected from the surface of the first and second plane members illuminated by the light source;
- means for inferring a reference surface shape of said first plane member from the detected light reflected from the surface of the second plane member;
- means for calculating a surface shape of the first plane member from the detected light reflected from the surface of the first plane member;
- means for comparing the inferred reference surface shape and the calculated surface shape; and
- means for determining a surface-shape-defect of the first plane member using the result of the comparing.

32. A surface-shape-defect inspecting apparatus according to claim 31, wherein said first plane member has a lower rigidity than a rigidity of the second plane member.

33. A surface-shape-defect inspecting apparatus according to claim 32, wherein a periphery of said first plane member is rigidly fixed to the second plane member.

34. A surface-shape-defect inspecting apparatus according to claim 31, wherein said first plane member has holes in the surface thereof.

35. A surface-shape-defect inspecting apparatus for identifying a shape defect of a first plane member partly fixed to a second plane member, comprising:

- a light source which illuminates a surface of the first plane member;
- a detector which detects a light reflected from the surface of the first plane member illuminated by the light source;
- means for inferring a reference surface shape of said first plane member from a desired data of a surface of the second plane member;
- means for calculating a surface shape of the first plane member from the detected light reflected from the surface of the first plane member;
- means for comparing the inferred reference surface shape and the calculated surface shape; and
- means for determining a surface-shape-defect of the first plane member using the result of the comparing.

36. A surface-shape-defect inspecting apparatus according to claim 35, wherein said first plane member has a lower rigidity than a rigidity of the second plane member.

37. A surface-shape-defect inspecting apparatus according to claim 36, wherein a periphery of said first plane member is rigidly fixed to the second plane member.

38. A surface-shape-defect inspecting apparatus according to claim 35, wherein said first plane member has holes in the surface thereof.

* * * * *